United States Patent [19]

Allen

[11] 4,287,003
[45] Sep. 1, 1981

[54] STABILIZATION OF CHLORINATED ALIPHATIC HYDROCARBONS

[75] Inventor: Christopher S. Allen, Stockton-on-Tees, England

[73] Assignee: Imperial Chemical Industries Limited, London, England

[21] Appl. No.: 58,443

[22] Filed: Jul. 18, 1979

[30] Foreign Application Priority Data

Jul. 27, 1978 [GB] United Kingdom ............... 31314/78
Jul. 27, 1978 [GB] United Kingdom ............... 31316/78

[51] Int. Cl.³ .................. B08B 3/08; C07C 17/42; C11D 7/50; C23G 5/02
[52] U.S. Cl. ................................ 134/31; 134/40; 252/153; 252/162; 252/171; 252/172; 252/400 R; 252/541; 252/542; 570/116
[58] Field of Search .................. 134/31, 40; 252/153, 252/162, 171, 172, 400 R, 407; 260/652.5 R

[56] References Cited

U.S. PATENT DOCUMENTS

| | | | |
|---|---|---|---|
| 2,094,367 | 9/1937 | Missbach | 260/652.5 R |
| 2,364,588 | 12/1944 | Morris | 260/652.5 R |
| 2,671,064 | 3/1954 | Cowell | 260/652.5 R |
| 2,964,485 | 12/1960 | Martinelli | 260/652.5 R |
| 3,397,246 | 8/1968 | Ryckaert | 260/652.5 R |
| 3,723,332 | 3/1973 | Barton | 252/171 |

FOREIGN PATENT DOCUMENTS

| | | | |
|---|---|---|---|
| 596258 | 4/1960 | Canada | 260/652.5 R |
| 1221250 | 2/1971 | United Kingdom | 260/652.5 R |

*Primary Examiner*—Dennis L. Albrecht
*Attorney, Agent, or Firm*—Cushman, Darby & Cushman

[57] ABSTRACT

Trichloroethylene, perchloroethylene or methylene dichloride is stabilized with an epoxy alkyl ester which is derived from a carboxylic acid containing from 5 to 22 carbon atoms and from an alcohol containing from 3 to 12 carbon atoms.

12 Claims, No Drawings

STABILIZATION OF CHLORINATED ALIPHATIC HYDROCARBONS

This invention relates to the stabilisation of chlorinated aliphatic hydrocarbons containing 1 to 2 carbon atoms.

Trichloroethylene is employed on a large scale for the degreasing of metal and other articles. Perchloroethylene is also employed to a considerable extent for such purposes and to a lesser extent so is methylene chloride. These solvents are fairly stable but by no means completely so. This instability increases at elevated temperatures which are encountered for example in the vapour degreasing of metals. Thus autoxidation of the solvents occur with generation of hydrogen chloride and there can be attack by metal and/or metal salts on the solvents.

We have now found that certain epoxidised esters or stabilising compositions which include said epoxidised esters are effective in reducing decomposition of trichloroethylene, perchloroethylene and methylene chloride.

According to the present invention there is provided trichloroethylene, perchloroethylene or methylene chloride stabilised by an epoxy alkyl ester derived from carboxylic acids containing 5 to 22 carbon atoms and from alcohols containing 3 to 12 carbon atoms.

Preferably the acids from which the esters are derived contain 12 to 20 carbon atoms, for example 18 carbon atoms.

The preferred alcohols contain 3 to 8 carbon atoms.

By the term "epoxy alkyl ester" we mean those compounds wherein an epoxy group is introduced into the alkyl group of the alcohol and/or into the alkyl group of the carboxylic acid from which the ester is derived.

The alkyl ester may be derived from a carboxylic acid containing an n-alkyl, iso-alkyl, or cycloalkyl group and from an alcohol which contains a n-alkyl, iso-alkyl, alkenyl, cycloalkyl group or a polyol.

Examples of epoxy alkyl esters include epoxy octyl stearate and epoxy butyl stearate. Mixture of epoxy alkyl esters can be employed. Diepoxy cycloalkyl esters may also be used.

Mixtures of epoxy esters whereof the esters are derived from long chain acid and glycerols are also useful. Such esters occur in epoxidised vegetable oil, for example in epoxidised soya bean oil and epoxidised linseed oil. Such epoxidised oils consisting in part of epoxidised esters are included within the scope of the present invention as stabilisers for said three chlorinated aliphatic hydrocarbon solvents.

Quite small proportions by weight for example of the epoxy alkyl esters or the epoxidised vegetable oil, for instance, 0.05% by weight or less with reference to the solvent have a stabilising effect. Usually the proportion of the epoxy ester is not greater than 5% with reference to the solvent. Good results can be obtained for example when using 0.1% to 3% by weight of said ester with respect to the solvent.

Other known stabilisers for said three chlorinated aliphatic hydrocarbons may also be associated with the present novel stabiliser. For example useful results can be obtained when there are also incorporated in the trichloroethylene stabilising amounts of one or more of the following groups of conventional stabilisers for said solvent, namely, alkyl esters, phenols, amines, aliphatic monoketones, nitroalkanes, pyrrole derivatives including N-methyl pyrrole, hydrocarbons including olefinic hydrocarbons, for example, diisobutylene. Good results can also be obtained when there is incorporated in perchloroethylene a stabilising amount of a conventional stabiliser for said solvent, for example, a substituted phenol. Likewise good results can be obtained when there is incorporated in methylene chloride a stabilising amount of conventional stabilisers for said solvent, for example, alcohols or an olefinic hydrocarbon.

Each of these known stabilisers is usually present in an amount not greater than 4% by weight of the solvent. Indeed considerably smaller amounts of said conventional stabilisers can be used if desired.

In the present invention there may be provided concentrated solutions of the epoxidised ester in said three chlorinated aliphatic hydrocarbons in which the proportions by weight of the epoxidised ester are much greater than the aforesaid 5% by weight. These solutions may contain 20% to 70% by weight of epoxy alkyl esters for example, epoxy butyl stearate or epoxidised vegetable oil with reference to the solvent. By adding such concentrate to pure solvent or solvent depleted in said epoxidised ester content there can be produced solvent containing desired smaller amounts of the epoxidised ester which can then be used directly for cleaning of metals or for other purposes. Likewise concentrates may be utilised which contain not only a high proportion by weight of said epoxidised ester but also a high proportion of a conventional stabiliser or stabilisers.

The present invention includes within its scope a method of inhibiting decomposition of trichloroethylene, perchloroethylene or methylene chloride which comprises incorporating in said solvents said epoxy alkyl esters.

The invention also includes a method of degreasing, particularly vapour degreasing of metal and other articles which comprises bringing the articles into contact with trichloroethylene, perchloroethylene or methylene chloride containing said epoxy alkyl esters.

The following Examples illustrate the invention. Where parts and percentages are mentioned they are by weight.

EXAMPLE 1

To 100 mls each of trichloroethylene, perchloroethylene and methylene chloride were added 2% of an epoxidised linseed oil known under the Trade Mark 'Edenol' B316 (available commercially from Henkel and Co). These stabilised solvent mixtures were placed in glass stoppered, 250 ml, conical flasks. The flasks were placed at a distance of 25 cms (measured from their respective centres) from a source of ultraviolet light (400 w). After 14 days exposure to the light the solvents were analysed for acidity developed and for chloride ion. The results are given in Table 1. Acidity was determined if present by titration with $N/10$ sodium hydroxide solution and is expressed as hydrochloric acid. The chloride ion if present was determined by titration with $N/100$ silver nitrate solution.

TABLE 1

| Trichloroethylene | | Perchloroethylene | | Methylene Chloride | |
|---|---|---|---|---|---|
| Acidity as HCl ppm | $Cl^-$ ppm | Acidity as HCl ppm | $Cl^-$ ppm | Acidity as HCl ppm | $Cl^-$ ppm |
| NIL | NIL | NIL | NIL | NIL | NIL |

By way of comparison the experiments were repeated with unstabilised trichloroethylene, unstabilised perchloroethylene and unstabilised methylene chloride.

Further comparitive experiments were carried out with trichloroethylene, perchloroethylene and methylene chloride each containing 2% of a conventional stabiliser, namely, 1,2-butylene oxide. The results are given in Table II.

TABLE II

| STABILIZER | Trichloroethylene Acidity as HCl ppm | Trichloroethylene Cl⁻ ppm | Perchloroethylene Acidity as HCl ppm | Perchloroethylene Cl⁻ ppm | Methylene Chloride Acidity as HCl ppm | Methylene Chloride Cl⁻ ppm |
|---|---|---|---|---|---|---|
| NIL | 1665 | 1026 | 1944 | 1308 | 867 | 747 |
| 2% 1,2-butylene oxide | 1260 | 711 | 45 | 25 | 58 | 45 |

EXAMPLE 2

200 ml samples of trichloroethylene, perchloroethylene and methylene chloride each containing 2% of the epoxidised linseed oil described in Example 1 were submitted to an accelerated oxidation test specified in British Standard 580: 1963. Briefly this test comprised bubbling oxygen through the samples placed in a conical flask. The latter contained polished cleaned mild steel strips (51×13×1.5 mm) suspended in the vapour phase above the samples and similar mild steel strips (19.5×6.5×1.5 mm) placed below the surface of the liquid samples. The flask was surmounted by a water-cooled condenser via a glass joint.

The contents of the flask were heated continuously by means of an electric light bulb for 48 hours under reflux conditions (condensation of the vapours occurred in the lower half of the condenser). Portions of the samples were cooled to room temperature, approximately (68° F.), shaken with distilled water and titrated (if acid to bromophenol blue indicator) with sodium hydroxide solution to determine acidity as HCl ppm.

The results are given in Table III.

TABLE III

| Trichloroethylene Acidity as HCl ppm | Perchloroethylene Acidity as HCl ppm | Methylene Chloride Acidity as HCl ppm |
|---|---|---|
| 1000:2000 | NIL | NIL |

By way of comparison the experiments were repeated with essentially unstabilised trichloroethylene, unstabilised perchloroethylene and unstabilised methylene chloride. By essentially unstabilised trichloroethylene is meant trichloroethylene minimally stabilised with 0.02% triethylamine and is designated in Table IV as NIL. Further experiments were carried out with trichloroethylene, perchloroethylene and methylene chloride stabilised with a conventional stabiliser, namely, 1,2-butylene oxide. The results showing high and erratic figures for acidity for trichloroethylene are given in Table IV.

TABLE IV

| STABILIZER | Trichloroethylene Acidity as HCl ppm | Perchloroethylene Acidity as HCl ppm | Methylene Chloride Acidity as HCl ppm |
|---|---|---|---|
| NIL | 6700;20 000 3000;8000 | 1450 | 240 |
| 2% 1,2-butylene oxide | 4000;90 000 | 6 | 20 |

I claim:

1. A method of degreasing metal and other articles which comprises bringing the articles into contact with a solvent selected from the group consisting of trichloroethylene, perchloroethylene and methylene chloride in the vapor phase wherein said solvent has been stabilized with a stabilizing amount of an epoxy alkyl ester which is derived from a carboxylic acid containing 5 to 22 carbon atoms and from an alcohol containing 3 to 12 carbon atoms.

2. A method according to claim 1 wherein said solvent further contains a conventional stabilizer.

3. A method as claimed in claim 1 wherein the ester is derived from an acid containing 12 to 20 carbon atoms.

4. A method as claimed in claim 1 or claim 3 wherein the ester is derived from an alcohol containing from 3 to 8 carbon atoms.

5. A method as claimed in claim 1 in which the ester is derived from a carboxylic acid containing an n-alkyl, iso-alkyl or cyclo-alkyl group and from an alcohol containing an n-alkyl, iso-alkyl, alkenyl, cyclo-alkyl group or a polyol.

6. A method as claimed in claim 1 or claim 5 in which the stabilizer for the solvent is a mixture of epoxy alkyl esters derived from long chain fatty acids and glycerol.

7. A method as claimed in claim 6 in which the stabilizer for the solvent is an epoxidized vegetable oil.

8. A method as claimed in claim 7 in which the stabilizer for the solvent is an epoxidized soya bean oil.

9. A method as claimed in claim 7 in which the stabilizer for the solvent is an epoxidized linseed oil.

10. A method as claimed in claim 5 in which the proportion by weight of epoxy alkyl ester is about 0.05% to about 5% by weight with reference to the solvent.

11. A method as claimed in claim 1 or claim 5 in which the solvent is trichloroethylene.

12. A method as claimed in claim 11 in which there is also incorporated in the solvent a stabilizing amount of one of more of the following conventional stabilizers therefor: phenols, amines, aliphatic monoketones, nitroalkanes, pyrolle derivatives and olefinic hydrocarbons.

* * * * *